United States Patent [19]

Herbert et al.

[11] 3,983,870

[45] Oct. 5, 1976

[54] SLIP RESISTANT BODY LIMB SUPPORT AND METHOD OF PREPARATION

[75] Inventors: John Henry Herbert, White Bear Lake; John Fred Vanderlouw, Woodbury, both of Minn.

[73] Assignee: Minnesota Mining and Manufacturing Company, St. Paul, Minn.

[22] Filed: Apr. 21, 1975

[21] Appl. No.: 569,870

[52] U.S. Cl. .................................. 128/165; 2/240; 427/243; 428/253
[51] Int. Cl.² .................. A61F 13/00; A41B 11/02
[58] Field of Search .............. 2/240, 239; 428/253; 128/165, 87 R, 87 A; 427/236, 237, 243, 171

[56] References Cited
UNITED STATES PATENTS

| | | |
|---|---|---|
| 1,358,799 | 11/1920 | Tully .................................. 2/240 X |
| 2,050,156 | 8/1936 | Borghetty .......................... 2/240 X |
| 2,666,208 | 1/1954 | Funk .................................. 2/239 X |
| 2,996,726 | 8/1961 | Mayer ................................. 2/240 |

*Primary Examiner*—H. Hampton Hunter
*Attorney, Agent, or Firm*—Alexander, Sell, Steldt & DeLaHunt

[57] ABSTRACT

A body limb support comprising a limb encircling member comprising knitted thread wherein the outer parts of the knitted thread in a relaxed state on a substantial portion of the inner surface of the limb encircling member have attached thereto a nonadhesive, noncontinuous, relatively soft, elastomeric polymeric material with a high coefficient of friction to skin so as to provide a nonocclusive slip resistant surface capable of maintaining the support in place on the limb of the body.

15 Claims, 5 Drawing Figures

SLIP RESISTANT BODY LIMB SUPPORT AND METHOD OF PREPARATION

This invention relates to a slip-resistant body limb support. Particularly, this invention relates to stockings wherein the leg portion of the stocking has coated on the outer parts of the knitted thread of the inner surface thereof polymeric material with a high coefficient of friction to skin.

Maintaining supports such as stockings in place on limbs such as the leg has been a problem for years because the supports tend to move from position on the limb. Specifically, stockings tend to, during use, creep down the leg. The over-the-calf type stockings and thigh-length stockings have been particularly troublesome. With stockings which are being worn mainly for aesthetic purposes or to keep the feet and legs warm, support being secondary, this in an annoyance which is not necessarily detrimental to the health. However, with elastic support stockings it is critical that the stockings stay in place so that the full value of the stocking can be realized.

Two typical types of stockings are anti-embolism stockings which are used to prevent emboli or blood clots in legs of bed-ridden patients and stockings used to treat persons afflicted with varicose veins. These stockings apply carefully controlled pressure to the leg with pressure decreasing from the foot to the top of the stocking. It is critical that they be maintained in position on the leg in order for the anti-embolism effect to be present and in order that appropriate support be maintained on the legs and veins therein.

Many attempts have been made to remedy the slippage problem with stockings. "Stiffening elements" have been added to the boot portion of the stocking in order to maintain it in place. These stiffening elements were strips of the stocking which had been coated with a solution of vinyl acetate or vinyl chloride in order to stiffen the fibers in that area of the stocking (U.S. Pat. No. 2,283,278). Rubber rings have been placed around the welt of the stocking in order to hold it in place (U.S. Pat. No. 2,514,108). Nylon hosiery has been treated by dipping it in a solution containing silica and, optionally, charged synthetic resin particles to increase resistance to slippage (U.S. Pat. No. 2,701,218). Tacky adhesive applied to the welt of the stocking has been used (U.S. Pat. No. 3,662,760). Slip resistant threads have been used as part of the knitted fabric (U.S. Pat. Nos. 3,392,553 and 3,800,331). Polyurethane or casein and latex has been applied to certain areas of a stocking to resist slippage and bagging and twisting of the stocking (U.S. Pat. No. 3,996,726).

None of the above attempts have resulted in an acceptable stocking. The stockings (a) had occlusive portions, (b) were stiff, (c) applied pressure to too small an area thus, restricting blood flow, (d) were adhesive and/or (e) did not provide adequate slip resistance.

Applicants have discovered a body limb support, particularly a stocking which does not have the aforesaid problems. The body limb support comprises a limb encircling member comprising knitted thread having a nonadhesive, noncontinuous, relatively soft, elastomeric polymeric material with a high coefficient of friction to skin attached to the outer parts of the knitted thread in a relaxed state on a substantial portion of the inner surface of the limb encircling member, the polymeric material comprising a non-occlusive slip-resistant surface capable of maintaining the support in place on the limb of the body.

A process for preparing a nonocclusive slip-resistant body limb support comprising a limb encircling member comprising knitted thread is also provided. The process comprises applying an elastomeric polymeric material having a high coefficient of friction to skin capable of drying to a nonadhesive state onto the outer parts of the knitted thread in a relaxed state on a substantial portion of the inner surface of the limb encircling member and drying said polymeric material on said thread.

While the support of the present invention can be applied to the arms, fingers, and head, etc., it is particularly useful as a stocking. In the case of the stocking the support is the stocking and the limb encircling member to which the polymeric material is applied is the leg portion of the stocking.

Normally there are two types of stockings upon which the polymeric material will be applied. These are those that extend to just below the knee and those which are thigh-length, that is, extend past the knee and onto the thigh of the wearer.

The invention will be described in more detail by reference to stockings and with reference to the following drawings in which.

Figure 1:
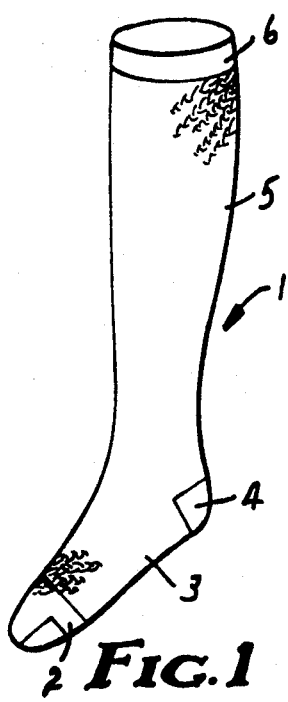
FIG. 1 depicts a knee-length stocking.

Referring in more detail to the drawings, stocking 1 of FIG. 1 comprises a toe 2, foot 3 extending from toe 2 to heel 4, heel 4, boot 5 extending from the heel 4 to the welt 6 and welt 6. The foot portion of the stocking as used herein comprises foot 3 and can include the toe 2 and heel 4. The leg portion of the stocking as used herein comprises the boot 5 and welt 6. The welt 6 is normally a turned over portion of the knitted thread which is stitched to itself. The stocking shown is knee-length but the same nomeclature is applicable to the thigh-length stocking wherein the boot would merely be longer and possibly of a different circumference.

Figure 2:
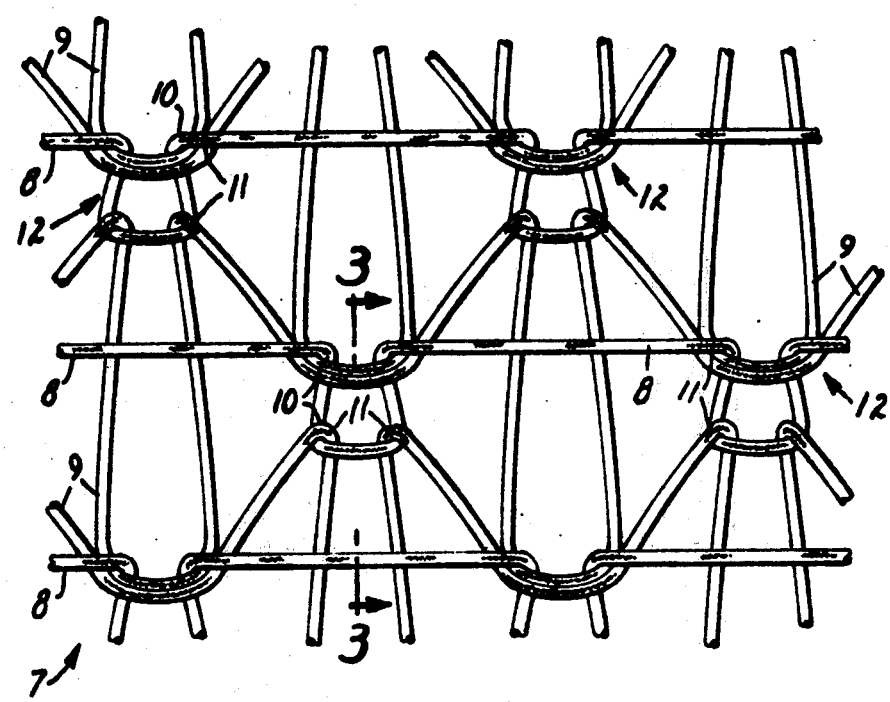
FIG. 2 is an enlarged view of the knitted thread of the inner surface of the leg portion of the stocking with the polymeric material applied thereto.

FIG. 2 depicts an enlarged view of the knitted thread of the boot of the stocking of the present invention with the polymeric material attached thereto. Specifically, FIG. 2 is a greatly enlarged view of the inner surface of the knitted threads 7 of the stocking in their stretched configuration. The amount of stretching shown is greater than that of the stocking in normal use and is shown in this fashion so that the threads could be more easily seen. Two types of threads are shown. These are spandex type threads 8 which contain an elastomeric core with nylon filaments (not shown in detail) would around them and nylon thread 9 knitted with the spandex threads. Both types of threads stretch since the spandex threads 8 contain an elastomeric core and the nylon thread 9 is texturized. The threads 8, 9 are coated on the outer parts 10 of the inner surface of the stocking by polymeric material 11. As shown, the threads 8, 9 have the polymeric material 11 covering from about 20 to 30 percent of the visible surface of the threads 8, 9. This is true because the application of the polymeric material to the knitted thread 7 takes place when the threads 8, 9 are in a relaxed state; thus, the knit points 12 are adjacent to each other and a large percentage of the threads 8, 9 visible in the stretched configuration of FIG. 2 are not visible and not contacted by the polymeric material 11 during its application. In the relaxed condition of threads 8, 9 the knit points 12 generally form the outer parts. Therefore, threads which, in FIG. 3, a section view taken along line 3--3, do not appear to be necessarily outer in the stretched state, are outer in the relaxed state.

Figure 3:
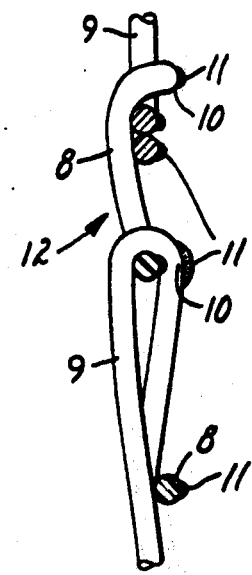
FIG. 3 is a section taken along line 3—3 of that depicted in FIG. 2.

FIG. 3 shows more clearly the overlap of the threads in a knit point 12 and the relative positions of the threads 8, 9 and polymeric material 11.

Normally at least 50 percent, preferably at least 90 percent of the inner surface of the leg portion of the knee-length stocking has polymeric material on the outer parts of the knitted threads in the relaxed state. This amount of coverage by the polymeric material produces a large area of slip resistance in the inner surface of the stocking. With the thigh-length stocking, normally at least that part of the leg portion of the stocking above the knee will have the polymeric material thereon.

The polymeric material normally covers at least about 90 percent of the outer parts of the knitted thread in the relaxed state in the area where the polymeric material is applied. Upon stretching to the normal use position only about 30 percent of the visible surface of the threads will be coated and the gaps between the threads are not filled with polymeric material. Therefore, the stocking is not stiff and is not occlusive.

The stocking depicted in the figures is an elastic support stocking since it contains both spandex and nylon thread. While it is preferred to have elastomeric thread present, this is not required as long as the knitted thread structure stretches. Thus, the stockings can be normal stockings with the polymeric material applied thereto. Examples of useful threads include the spandex types, e.g., Lycra spandex rubber, E. I. duPont de Nemours and Company, Wilmington, Del. and Glospan spandex rubber, Globe Manufacturing Co., Fall River, Mass. 02772; cotton; polypropylene; rayon; polyester; and nylon. These can be used singly or in combination. Normally if spandex is used it will be used with another type thread such as texturized nylon. The spandex thread can be wrapped with other thread or filaments or can consist of the elastomeric filament singly.

As depicted, the stocking has, among other things, a heel, toe and foot. The stocking without a heel and toe can be utilized and the therapeutic effect obtained. Supports for the legs which do not include a foot portion can also be used. Thus, a generally cylindrical member of knitted thread can be used. For use on limbs other than the leg such as the arms, hands and head, the support normally comprises a generally cylindrical shape of knitted thread with the polymeric material on the outer parts of the knitted thread on a substantial portion of an inner surface of the generally cylindrical member.

The supports can be used to generally support a limb, prevent the formation of emboli, treat varicose veins or to hold a wound compress or bandage in place on a limb. They can also be used as a limb isolation drape.

The polymeric material useful in the support, specifically the stocking, is generally the rubber-like materials including natural rubber and synthetic polymers. These have a high coefficient of friction to skin; low hardness, i.e., a Shore A hardness of from about 20 to about 70 (ASTM D-224068); a torsional modulus (at 300 kgm/cm$^2$) of less than about 0°C., preferably less than −5°C. (ASTM D-1043-72 or ASTM D-1053-73); and are elastomeric, that is, they can be stretched repeatedly to at least twice their original length. Examples of useful polymeric materials include acrylic polymers, vinyl chloride polymers, vinyl chloride/vinylidene chloride polymers, vinyl chloride/acrylic polymers, butadiene/acrylonitrile polymers, vinyl acetate/acrylic polymers, styrene/acrylic polymers, carboxylated styrene/butadiene polymers, styrene/butadiene polymers, vinylidene chloride/acrylic polymers, ethylene/vinyl acetate polymers, ethylene/ethyl acrylate polymers, ethylene/methylacrylate polymers, styrene/butadiene/styrene polymers, styrene/isoprene/styrene polymers, polyvinyl ethyl ether, and conventional thermoset elastomers of natural rubbers, polyisoprene, butadiene, chlorosulfonated polyethylene, nitrile, polyacrylates, urethanes, chloroprenes, chlorinated polyethylenes and the like.

Many of the polymeric materials listed are applied to the knitted stretch threads in the form of a latex, e.g., the acrylic polymers. Others can be applied in the form of a solution in a solvent. The solvent utilized must not be destructive to the threads of the support. Fast drying solvents such as cyclohexane, methylethylketone or heptane or mixtures thereof are normally used.

The prefered polymeric material is the acrylic polymers. These are normally contacted with the threads in the form of a latex. The film produced from the polymer is soft to intermediate. The latex is normally 30 to 50 percent by weight acrylic polymer and has a viscosity of from 35 to 600 centipoise at 25°C. (test defined below). The minimum film forming temperature of the polymer is less than 0°C. and the torsional modulus (at 300 kgm/cm$^2$) of the air-dried film is −50° to 0°C., preferably less than −5°C.

Normally the polymeric material is applied to the knitted thread by spraying a fine mist of a solution or latex of the polymeric material onto the knitted threads. The viscosity of the latex or solution is adjusted so that the particles of polymeric material partially dry while in transit to the thread; thus, when they contact the thread they are, while still tacky and therefore able to attach to the outer part of the thread, not so wet as to soak through the thread and into the thread below. Such soaking or saturation of the thread structure can result not only in a stiff limb encircling member but in a limb encircling member which is occlusive. With the latexes, the solids content is normally from about 30 to about 50 percent by weight of the latex; while with the solvent solution of the polymeric material the solids concentration in the solvent is normally about 5 to 15 percent by weight. The solids concentration will vary depending on the type of polymer used and solvent used. Lesser concentrations are capable of being used in the solvent system because the solvents normally volatilize much more rapidly than water.

The polymers can be plasticized if necessary to obtain a rubbery, high coefficient of friction type polymer. The plasticizer must be nontoxic, nonirritating and nonmigratory since the support is in contact with the skin.

Other means of applying the polymeric material to the knitted thread can be used such as dipping the knitted thread so that only the outer part of the inner surface contacts the polymeric material or brushing or rolling the solution or latex of the polymeric material onto the outer parts of the threads in such a fashion so that saturation and soaking does not occur. These methods, while possible are not preferred since it is very difficult to control the application of the polymeric material when using these methods.

Generally, 0.002 to 0.015 gm/in² (0.00031 to 0.00232 gm/cm²), preferably 0.006 to 0.009 gm/in² (0.00093 to 0.00139 gm/cm²) of polymeric material will be attached to the knitted thread in the relaxed state of the support of the invention.

The following example is meant to illustrate but not to limit the invention. Parts and percentages are by weight unless otherwise specified.

EXAMPLE

Several knee-length elastic support stockings from Grey Hosiery, Inc., Asheboro, N.C. having the knit configuration shown in FIG. 2 wherein thread 8 was Glospan spandex rubber and thread 9 was texturized nylon were first supported on a rack which allowed for the spraying of one side of the inner surface of the stocking and then the other side of the inner surface of the stocking and also allowed for the stocking to be placed into a drying oven without direct handling of the sprayed stocking. The stockings were then sprayed on the inner surface of the leg portion thereof as will be discussed in detail below with Rhoplex HA-8 acrylic emulsion, Rohm & Haas Company, Philadelphia, Pa. Rhoplex HA-8 has the following properties:

| | |
|---|---|
| Appearance | milky white liquid |
| Film characteristics | soft, rubbery |
| Solids content | 45.5 percent by weight |
| pH | 3.0 |
| Specific gravity | 1.05 at 25°C. |
| Minimum film forming temperature | less than 0°C. |
| Viscosity measured on a Brookfield Viscometer (Brookfield Engineering Laboratories, Stroughton, Massachusetts, Brookfield, No. 3 spindle, 60 revolutions per minute) | 550 centipoises at 25°C. |
| Torsional modulus (300 kgm/cm²) | 14°C. |

The spray gun utilized was a Binks model 15, Binks Manufacturing Co., Franklin Park, Ill. 60130. The gun was equipped with an external mix air nozzle. An in-line filter extracter and regulator were used to purify and dry the 90 pounds per square inch line air (6.3 kg/cm²) and to reduce this pressure to the desired 40 pounds per square inch (2.8 kg/cm²) at the spray gun. The acrylic emulsion was under 10 to 12 pounds per square inch (0.7 to 0.8 kg/cm²) from a pressure-type fluid cup. These combinations of pressure from the fluid cup and air produced a dispersed pattern (atomized mist) of the emulsion from the Binks No. 78 air and No. 78 P fluid nozzles.

Substantially the entire inner surface of the leg portion of each stocking from ½ inch (1.3 cm) from the top to ½ inch (1.3 cm) above the heel pocket was sprayed by making two, 2½ second passes on each side of the inner surface of the stocking by a continuous motion longitudinally over the stocking. The knitted thread of the stocking was relaxed during spraying. The stockings were then dried at 160°F. (71°C.) for about 3 minutes and cured at 160°F. (71°C) for 16 hours. The coating weight on the stockings was found to be from about 0.007 to 0.008 grams per square inch (0.00108 to 0.00124 gm/cm²) when the knitted thread is in the relaxed state. The nonadhesive acrylic polymer was on the outer part of the knitted threads on the inner side of the leg portion of the stocking and the stocking was nonocclusive.

Some of the coated stockings were tested on an Instron model 1130 (Instron Corp., Canton, Mass) to measure the effect of the coating on the elastomeric properties of the stockings as follows:

Sample coated stockings were measured at the widest coated part of the calf and at the narrowest coated part of the ankle. Two 3 inch (7.6 cm) by 1 inch (2.5 cm) by ¼ inch (0.64 cm) metal bars with a 1/16 inch (0.16 cm) diameter metal rod, 2 inches (5 cm) long, positioned and attached to the middle of the 3 inch (7.6 cm) by ¼ inch (0.64 cm) side of the bars were used to stretch the stockings laterally. The rods were pushed through the knitted threads opposite each other at the areas above mentioned, one area at a time. The rods were positioned in the Instron jaws with the outer side of the metal bars 2¾ inches (7 cm) apart and touching the Instron crosshead jaws. The Instron was prepared by setting the crosshead and chart speeds at 10 inches (25.4 cm) per minute, spacing the crosshead jaws 2¾ inches (7 cm) apart at 0 inch (0 cm) gage length and setting the return selector to 6 inches (15.2 cm) when measuring at the calf and 4 inches (10.2 cm) when measuring at the ankle. Uncoated control samples of the same construction were measured in the same manner. Each size of stocking has a calf and ankle circumference range in which it will exert the sought after amount of force. The force exerted by the stockings was measured at a crosshead length equal to one-half of the mean of the size range for the size stocking being measured. The forces measured were translated into millimeters of mercury (mm Hg) pressure and are shown in the following table:

| Stocking Size | Tested Area | Control | | Coated | |
|---|---|---|---|---|---|
| | | Pressure | Circumference | Pressure | Circumference |
| Small | Calf | 11.8 mm Hg | 11.5 inches (29.2 cm) | 14.1 mm Hg | 11.5 inches (29.2 cm) |
| | Ankle | 14.4 mm Hg | 7.5 inches (19.1 cm) | 14.4 mm Hg | 7.5 inches (19.1 cm) |
| Medium | Calf | 14.0 mm Hg | 13.5 inches (34.3 cm) | 16.0 mm Hg | 13.5 inches (34.3 cm) |
| | Ankle | 15.9 mm Hg | 8.5 inches (21.6 cm) | 19.1 mm Hg | 8.5 inches (21.6 cm) |
| Large | Calf | 14.0 mm Hg | 15.5 inches (39.4 cm) | 15.7 mm Hg | 15.5 inches (39.4 cm) |
| | Ankle | 18.5 mm Hg | 9.5 inches (24.1 cm) | 19.9 mm Hg | 9.5 inches (24.1 cm) |

The differences in results obtained with the control versus coated stockings were not considered to be significant for the intended use of the stocking.

The slip characteristics of the stockings were also tested. Six evaluators wore one coated stocking and one uncoated control stocking. Each stocking was measured for slippage after 4 and 6 hours of wear. This procedure was repeated 1 day later with the stockings switched to the opposite legs of the same subject. This entire procedure was repeated after one machine washing and drying. Each subject wore the same pair of stockings all 4 days. The average slippage taken from the results given below was 4.0 inches (10.2 cm) for the untreated control stockings and 0.6 inch (1.5 cm) for the treated stockings. A reading of 6 plus inches means the stocking slipped down to the ankle.

| Subject (human) | SIZE Calf circumference | stocking | DAY I Control 4 hour | 6 hour | Treated 4 hour | 6 hour | DAY II Control 4 hour | 6 hour | Treated 4 hour | 6 hour |
|---|---|---|---|---|---|---|---|---|---|---|
| 1 | 13.0 in. (33.0 cm) | Small | 2.5 in (6.4 cm) | 2.75 in (7 cm) | 1.5 in (3.8 cm) | 1.5 in (3.8 cm) | 0.5 in (7.6 cm) | 3 in (7.6 cm) | 0.5 in (1.3 cm) | 0.75 in (1.9 cm) |
| 2 | 12.5–13.0 in (31.8–33.0 cm) | Small | 2 in (5.1 cm) | 2.25 in (5.7 cm) | 0.25 in (0.6 cm) | 0.5 in (1.3 cm) | 5 in (12.7 cm) | — | 0.75 in (1.9 cm) | — |
| 3 | 14.5 in (36.8 cm) | Medium | — | 3 in (7.6 cm) | — | 1 in (2.5 cm) | 6+ in (15.2 cm) | 6+ in (15.2 cm) | 0.75 in (1.9 cm) | 1 in (2.5 cm) |
| 4 | 14.5–14.75 in (36.8–37.5 cm) | Medium | 2.25 in (5.7 cm) | 2.75 in (7.0 cm) | 0.25 in (0.6 cm) | 0.5 in (1.3 cm) | 6+ in (15.2 cm) | 6+ in (15.2 cm) | 0.25 in (0.6 cm) | 0.25 in (0.6 cm) |
| 5 | 15.75–16 in (40.0–40.6 cm) | Large | 1.5 in (3.8 cm) | 2.25 in (5.7 cm) | 0.25 in (0.6 cm) | 0.5 in (1.3 cm) | 5.75 in (14.6 cm) | 6+ in (15.2 cm) | 0.75 in (1.9 cm) | 0.75 in (1.9 cm) |
| 6 | 15.5–16 in (39.4–40.6 cm) | Large | 1 in (2.5 cm) | 1 in (2.5 cm) | 0.25 in (0.6 cm) | 0.5 in (1.3 cm) | 2.5 in (6.4 cm) | 3 in (7.6 cm) | 0.5 in (1.3 cm) | 0.75 in (1.9 cm) |
|  |  | Average | 1.9 in 4.8 cm | 2.3 in 5.8 cm | 0.5 in 1.3 cm | 0.9 in 2.3 cm | 4.7 in 11.9 cm | 4.8 in 12.2 cm | 0.6 in 1.5 cm | 0.6 in 1.5 cm |

| SUBJECT (human) | SIZE Calf circumference | stocking | DAY III Control 4 hour | 6 hour | Treated 4 hour | 6 hour | DAY IV (after washing) Control 4 hour | 6 hour | Treated 4 hour | 6 hour |
|---|---|---|---|---|---|---|---|---|---|---|
| 1 | 13.0 in (33 cm) | Small | 2.75 in (7.0 cm) | 2.75 in (7.0 cm) | 1.25 in (3.2 cm) | 1.25 in (3.2 cm) | 3 in (7.6 cm) | 3 in (7.6 cm) | 0.5 in (1.3 cm) | 0.75 in (1.9 cm) |
| 2 | 12.5–13 in (31.8–33 cm) | Small | 4 in (10.2 cm) | 5 in (12.7 cm) | 0.25 in (0.6 cm) | 0.5 in (1.3 cm) | 4 in (10.2 cm) | 6 in (15.2 cm) | 0 | 0 |
| 3 | 14.5 in (36.8 cm) | Medium | 2 in (5.1 cm) | 6+ in (15.2 cm) | 0 | 0 | — | 6+ in (15.2 cm) | — | 1.5 in (3.8 cm) |
| 4 | 14.5–14.75 in (36.8–37.5 cm) | Medium | 6+ in (15.2 cm) | 6+ in (15.2 cm) | 0.25 in (0.6 cm) | 0.25 in (0.6 cm) | 6+ in (15.2 cm) | 6+ in (15.2 cm) |  |  |
| 5 | 15.75–16 in (40–40.6 cm) | Large | 4 in (10.2 cm) | 6+ in (15.2 cm) | 1.25 in (3.2 cm) | 1.50 in (3.8 cm) | 6+ in (15.2 cm) | 6+ in (15.2 cm) | 0.75 in (1.9 cm) | 1 in (2.5 cm) |
| 6 | 15.5–16 in (39.4–40.6 cm) | Large | 4.25 in (10.8 cm) | 5.25 in (13.3 cm) | 0.75 in (1.9 cm) | 0.75 in (1.9 cm) | 1.75 in (4.4 cm) | 1.75 in (4.4 cm) | 0.25 in (0.6 cm) | 0.25 in (0.6 cm) |
|  |  | Average | 3.8 in (9.7 cm) | 5.2 in (13.2 cm) | 0.6 in (1.5 cm) | 0.7 in (1.8 cm) | 4.2 in (10.7 cm) | 4.8 in (12.2 cm) | 0.3 in (0.8 cm) | 0.6 in (1.5 cm) |

We claim:

1. A body limb support comprising a limb encircling member comprising knitted thread having a nonadhesive, non-continuous, relatively soft, elastomeric polymeric material with a high coefficient of friction to skin attached to the outer parts of the knitted thread in a relaxed state on a substantial portion of the inner surface of the limb encircling member, the polymeric material comprising a nonocclusive, slip resistant surface capable of maintaining the support in place on the limb of the body.

2. The body limb support of claim 1 wherein said knitted thread comprises elastomeric thread.

3. The body limb support of claim 1 wherein at least 50 percent of the inner surface of the limb encircling member has polymeric material attached to the outer parts of the knitted thread in a relaxed state.

4. The body limb support of claim 1 wherein at least 90 percent of the inner surface of the limb encircling member has polymeric material attached to the outer parts of the knitted thread in a relaxed state.

5. The body limb support of claim 1 wherein the polymeric material is acrylic polymer.

6. A stocking comprising a foot portion and a leg portion comprising knitted thread having a nonadhesive, noncontinuous, relatively soft, elastomeric polymeric material with a high coefficient of friction to skin attached to the outer parts of the knitted thread in a relaxed state on a substantial portion of the inner surface of the leg portion of the stocking, the polymeric material comprising a non-occlusive, slip-resistant surface capable of maintaining the stocking in place on the leg of the body.

7. The stocking of claim 6 wherein said knitted thread comprises elastomeric thread.

8. The stocking of claim 7 wherein at least 50 percent of the inner surface of the leg portion of the stocking has polymeric material attached to the outer parts of the knitted thread in a relaxed state.

9. The stocking of claim 8 wherein the leg portion of the stocking extends from the ankle to the knee.

10. The stocking of claim 9 wherein at least 90 percent of the inner surface of the leg portion of the stocking has polymeric material attached to the outer parts of the knitted thread in a relaxed state.

11. The stocking of claim 7 wherein the leg portion extends from the ankle through the thigh and wherein at least 50 percent of the inner surface of the leg portion of the stocking has polymeric material attached to the outer parts of the knitted threads in a relaxed state.

12. The stocking of claim 6 wherein the polymeric material is acrylic polymer.

13. A process for preparing a nonocclusive, slip-resistant body limb support comprising a limb encircling member comprising knitted thread comprising applying an elastomeric, polymeric material having a high coefficient of friction to skin capable of drying to a nonadhesive state onto the outer parts of the knitted thread in a relaxed state of a substantial portion of the inner surface of the limb encircling member and drying said polymeric material on said thread.

14. The process of claim 13 wherein the polymeric material is applied by spraying the polymeric material onto said knitted thread.

15. The process of claim 14 wherein the polymeric material is sprayed in a fine mist and the particles of polymeric material in said mist are partially dry upon contact with said knitted thread.

* * * * *